United States Patent [19]

Phelps

[11] 4,278,225
[45] Jul. 14, 1981

[54] INCLINED VIAL HOLDER

[76] Inventor: Dennis B. Phelps, 4517 Vieja Dr., Santa Barbara, Calif. 93110

[21] Appl. No.: 72,015

[22] Filed: Sep. 4, 1979

[51] Int. Cl.³ .............................................. A47K 1/08
[52] U.S. Cl. ................................. 248/311.3; 211/88
[58] Field of Search ............... 248/311.2, 311.3, 313, 248/312; 222/181, 185; 211/88, 75, 73; 128/215

[56] References Cited

U.S. PATENT DOCUMENTS

| | | | |
|---|---|---|---|
| 773,366 | 10/1904 | Bennett | 248/312 X |
| 998,389 | 7/1911 | Penick | 222/185 |
| 1,349,842 | 8/1920 | McKinley | 248/313 |
| 1,624,830 | 4/1927 | Emsley | 248/311.2 X |
| 2,677,372 | 5/1954 | Barnish | 128/215 |
| 2,841,311 | 7/1958 | Parizek | 222/181 |
| 3,872,868 | 3/1975 | Kline | 248/312 X |
| 3,938,769 | 2/1976 | Wetherbee | 222/181 X |
| 3,945,060 | 3/1976 | Gargione | 222/181 X |
| 3,964,709 | 6/1976 | Labelle | 248/311.2 X |
| 3,982,716 | 9/1976 | Trees | 248/311.3 X |

*Primary Examiner*—J. Franklin Foss
*Attorney, Agent, or Firm*—Daniel J. Meaney, Jr.

[57] ABSTRACT

A holder for supporting a vial containing fluid therein in an inverted inclined position is shown. The holder includes a vertical back member adapted to be fastened to a wall and a planar top support extends from the backplate at a predetermined acute angle relative to a horizontal plane and has a length which is greater than the width of a vial. The planar top support receives and supports the bottom of the vial and produces a clamping force thereagainst. A planar bottom support extends from the vertical backplate at substantially the same acute angle as the planar top support and has a length equal to the distance from the backplate to a line which intersects with a plane which is normal to the end of the planar top support. The planar bottom support has an elongated slot to receive the neck of a vial and extends from the outer edge of the planar bottom support to an aperture extending through the planar bottom support. The aperture has a diameter which is slightly greater than the diameter of the neck of the vial. The planar top support and planar bottom support produce a clamping force between the bottom and shoulder of the vial to hold the same in a fixed inclined angle with the top thereof extending through the aperture of the holder to enable a user to insert a syringe into the top thereof.

16 Claims, 8 Drawing Figures

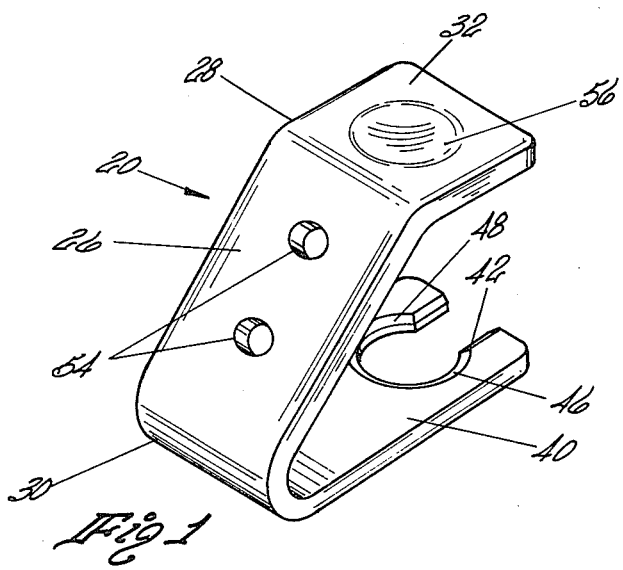
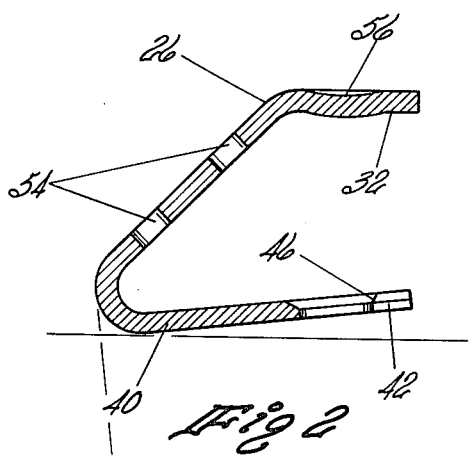
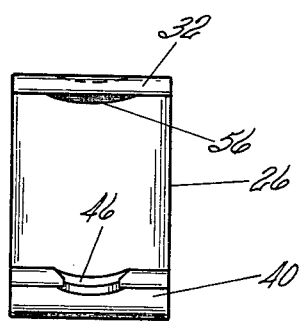
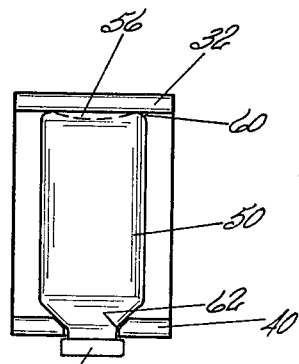
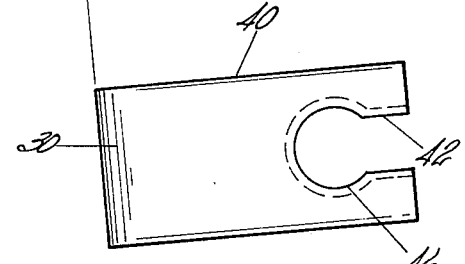
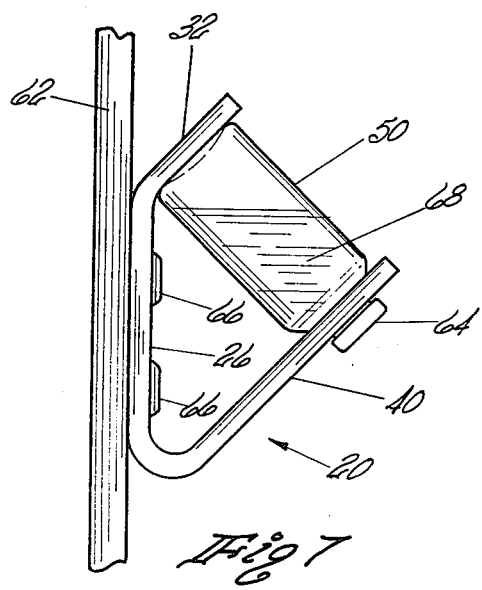
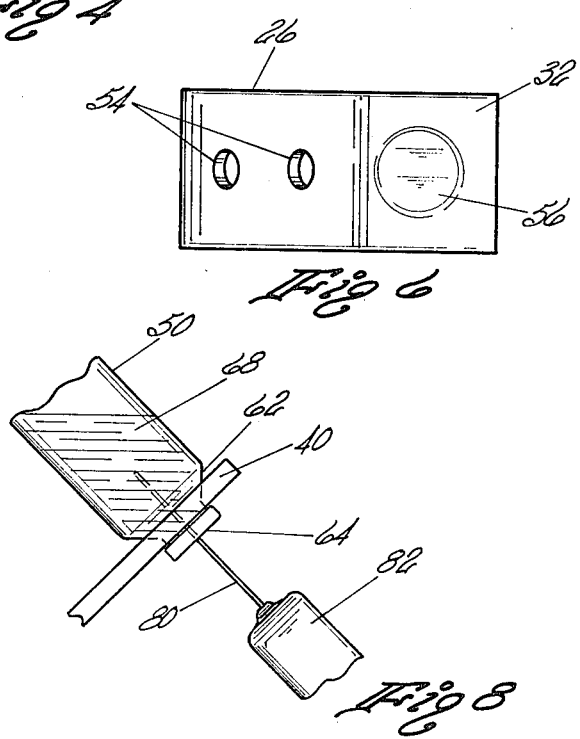

INCLINED VIAL HOLDER

BACKGROUND OF THE INVENTION

1. Field of the Invention

This invention relates to an inclined vial holder adapted to permit a user to insert a syringe therein to remove fluid from the inverted vial being held in an inclined angle and more particularly to an inclined bottle holder for supporting a vial of sterile fluid in an inverted clamped position wherein the vial can be easily removed and replaced and wherein the sterile fluid can be withdrawn from the vial by a syringe inserted into the top of the inverted vial held in an inclined position.

2. Description of the Prior Art

Medical bottle holders are known in the prior art. Typical of such devices is a bottle holder as described in U.S. Pat. No. 3,982,716 which discloses a medicine container comprising a hollow cylindrical body including a bottom end cover having an opening therein, a top cap, means for securing the top cap in position, and means for affixing the holder to a vertical wall. The medical bottle holder described in U.S. Pat. No. 3,982,716, holds the medical bottle in a vertically inverted position such, that the top extends through the opening in the bottom end cover so that both hands of a user are free to manipulate a syringe to withdraw the proper dosage from the bottle.

U.S. Pat. No. 2,513,029 discloses a bottle holder which is adapted for detachably supporting a bottle on a wall wherein the holder is formed of a cylindrical shaped housing having a removable top, a bottom having an opening which is adapted to hold a bottle in an inverted position and a holder which is adapted to support the cylindrical shaped housing with the bottle in an inverted position against the wall. Access to the bottom of the bottle is obtained by unscrewing and removing the bottom cover which permits access by a user to the top of the bottle to permit insertion of a syringe into the inverted top of the bottle to remove fluid therefrom.

U.S. Pat. No. 2,677,372 discloses a bottle holder assembly formed of a plurality of elements which include a support in the form of a flat planar surface, a neck clamping device which is adapted to engage the neck of a bottle and support the entire bottle and fluid in an inclined position such, that the top can have a hypodermic syringe inserted therein and a guide member which is adapted to guide a syringe towards the neck of the inclined bottle so as to permit insertion of the syringe through the top thereof to remove the sterile fluid from the bottle.

Each of the above-described devices include a plurality of separate elements in the form of cylindrical housings, caps, guide members, or other elements which result in a medical bottle holder formed as an assembly of such separate components.

In the bottle holders described in U.S. Pat. Nos. 3,982,716 and 2,513,029, the user must remove a top from the support housing, which usually requires unscrewing either a fastening member or the entire top in order to expose the interior of the cylindrical body. In use, a medicine bottle must be dropped in an inverted position into the housing in proper alignment such, that the neck and top of the bottle pass through the opening in the bottom of the housing. Further, in the medical bottle holders described in U.S. Pat. Nos. 3,982,716 and 2,513,029, the bottles are held in an inverted vertical position which makes access to the bottom while using a syringe extremely difficult. Further, in order to remove an empty medical bottle out of the holder by the neck and top, the bottle must be manipulated back through the opening in the bottom of the support and through the top of the cylindrical housing. This results in great difficulty in removing and inserting medical bottles of fluid into the holder and dropping of a full medicine bottle into the holder may damage the bottle if the neck and top thereof hit the edge of the bottom and do not properly align with the opening.

The bottle holder described in U.S. Pat. No. 2,667,372, clamps a portion of the neck of the bottle to support the entire bottle and fluid. This results in the entire supporting stress of the medical bottle and any stress imposed during insertion of the syringe being concentrated in the small portion of the neck of the bottle, which is typically the weakest area of the bottle. Further, the use of a guide member and other components, makes it difficult to provide easy access of a syringe to the bottle and requires the use of two hands to guide the syringe into the top of the inclined bottle. U.S. Pat. No. 2,667,372, discloses the use of other clamping means for clamping the entire neck of the bottle in position. Such clamping means apply stress to the neck of the bottle. Further, when a syringe is inserted into the bottle, additional stress is placed on the neck of the bottle due to the upward force inserted thereagainst by the syringe being transported over the guide member.

SUMMARY OF THE INVENTION

The present invention discloses a unique and novel holder for supporting a vial having a fluid therein in an inverted inclined angle. The vial has a top, neck, shoulder, and a bottom, and the holder holds the vial in an inverted position and at an inclined angle with the top of the vial freely extending through an opening in the bottom of the holder such, that a user can insert a syringe therein to remove the fluid from the vial which is held at an inclined angle. The inclined bottle holder includes a vertical backplate or back member which is adapted to be fastened to a vertical supporting surface such as a wall. The inclined vial holder has a relatively flat top support and a relatively flat bottom support, both of which are attached at an angle to the vertical backplate. The top support extends from the back support at an inclined angle measured from the horizontal plane which extends from the vertical back. The top support has a length which is sufficient to support the vial. The relatively flat bottom support is substantially coplanar with the relatively flat top support and extends from the vertical backplate at substantially the same acute angle. The length of the relatively flat bottom support is longer than that of the relatively flat top support, in that the flat bottom support has a length which is equal to the distance from the backplate to a line where the bottom support substantially intersects with a plane which is normal to the end of the relatively flat top support. The flat bottom support includes an elongated slot having a width which is adapted to receive and pass the neck of a vial. The elongated slot communicates with an aperture formed through the flat bottom support, which aperture is in substantial alignment with the center of the flat top support. In use, a vial is inserted into and clamped in position in the holder. Insertion of the inverted vial into the inclined bottle holder is accomplished by the neck being transported through the elongated slot to the aperture whereupon the relatively flat top support cooperates with the bottom support by a resilient action therebetween to clamp the vial by urging the bottle towards the bottom causing the shoulder of the vial to engage the flat bottom portion such, that the neck is passed through the aperture and entire vial and is held in a fixed inclined angle with the top of the vial freely extending from the flat bottom support and is adapted to have a user insert a syringe therein to remove fluid from the inverted vial being held at an inclined angle.

One advantage of the present invention is that a unitary inclined vial holder can be fabricated using the teachings of this invention. The inclined vial holder can be formed of a plastic material using known molding techniques which result in a low cost single element device. The elongated slot and aperture can be formed with relatively square edges or, if desired, the edges can be chamfered to smoothly slidably receive the vial.

Another advantage of the present invention is that a vial can be inserted with one hand into the device and the holder will firmly clamp and hold the vial in a sturdy inverted position. The entire clamping force is along the length of the vial which is the strongest part of the vial.

A further advantage of the present invention is that the acute angle relative to a horizontal plane is selected such, that when the fluid in the vial is nearly gone, the fluid remaining in the bottle resides in the neck thereof so that when a hypodermic syringe is inserted therein the remaining fluid can be withdrawn from the inclined vial.

A yet further advantage of the present invention is that the inclined vial holder can be firmly attached to a vertical supporting surface, for example, a wall, and the inclined vial can be easily accessible to a user, such as a physician having both hands covered with sterile gloves, to permit insertion of a syringe into the top thereof to remove the fluid from the vial without the necessity of the user using one of two hands to hold the vial. This avoids possible contamination of the sterile gloves by the glove touching the vial.

Another advantage of the present invention is that the label on the vial is visibly exposed to the user such, that the user can visually verify the contents of the vial at each withdrawal of fluid therefrom with a syringe.

A still further advantage of the present invention is that when a vial's contents have been completely used and the user has a syringe to be inserted in one hand, the user can use the other hand to remove the empty vial and easily and promptly replace the empty vial with a full vial of fluid by merely inserting the full bottle in the inverted position into the vial holder device.

This invention has utility in the medical and surgical fields or in other fields where it is necessary to use a hypodermic syringe. In the medical-surgical field, a doctor, nurse, or other appropriate individual can utilize the inverted vial holder as a support for medical sterile fluid and provide easy access thereof by use of the hypodermic syringe which can be inserted into the vial being held in an inclined angle. Other applications include electronic industries, where hypodermic syringes are used to dispense selected chemical coatings on surfaces or the like wherein the user requires access to a bottle of fluid for use in such applications.

BRIEF DESCRIPTION OF THE DRAWING

These and other advantages of the invention, together with its various features, can be more easily understood from the following more detailed description taken in conjunction with the accompanying drawing wherein:

FIG. 1 is a perspective view of an inclined vial holder of the present invention showing the preferred embodiment;

FIG. 2 is a front plan sectional view of an inclined vial holder showing that the flat top support and flat bottom support have a resiliency therebetween capable of producing a clamping action on an inverted vial;

FIG. 3 is a front plan view of the inclined vial holder of the present invention;

FIG. 4 is a front plan view of the inclined vial holder of the present invention showing the inverted vial held in a clamped position;

FIG. 5 is a bottom plan view of the inclined vial holder of the present invention showing the elongated slot and aperture;

FIG. 6 is a top plan view of the inclined vial holder of the present invention showing the preferred embodiment having a convex shaped surface on the flat top support;

FIG. 7 is a diagrammatic view showing an inclined vial holder attached to a vertical supporting surface and showing a clamped inverted vial being supported thereby; and FIG. 8 is an exploded detailed view showing the relationship between the bottom support, the top of a vial, and a hypodermic syringe being inserted into the top of a vial.

DESCRIPTION OF THE PREFERRED EMBODIMENT(S)

The inclined vial holder of the present invention is generally designated as 20 in FIG. 1. The inclined vial holder 20 includes a vertical backplate 26 which has a top edge 28 and a bottom edge 30. The vertical backplate 26 is adapted to be fastened to a vertical supporting surface, such as a wall, cabinet, or other similar support.

The inclined vial holder 20 includes a relatively flat top support 32 which is fastened to the top 28 of the vertical backplate 26 at a predetermined acute angle measured from a horizontal plane which intersects with the vertical backplate 26. The flat top support 32 has a length which is equal to or greater than the width of a vial, such as vial 50 shown in FIG. 4, which is to be supported thereby.

The flat top support 32 has some resiliency and is adapted to produce a clamping force against the bottom of the vial 50.

The inclined vial holder 20 includes a relatively flat bottom support 40 which is fastened to the bottom edge 30 of the vertical backplate 26. The flat bottom support extends from the vertical backplate 26 at substantially the same acute angle from the horizontal plane which is normal to the intersection of the vertical backplate 26 as that of the flat top support 32. The flat bottom support 40 is substantially in spaced parallel alignment with the flat top support 32.

The flat bottom support 40 has a length which extends a distance from the intersection of the flat bottom support 40 with edge 30 of the vertical backplate 26 to an outer edge which is located at the intersection of a line with a plane which is normal to the end of the flat top support 32. The flat bottom support has an elongated slot 42 and aperture 46 formed therein. In the preferred embodiment, the edge of the slot 42 and aperture 46 may be chamfered edges 48 to enable the vial to be better supported during insertion, clamping, and removal. If desired, mounting holes 54 may be provided using fasteners to attach the inclined vial holder 20 to a supporting surface. The flat top support 32, in the preferred embodiment, has a convex shaped surface under surface 56 to provide a positive point clamping force on the bottom of the vial. In the embodiment illustrated herein, the convex shaped undersurface 56 is formed by means of an indentation in the top support. Several methods may be used for forming the convex shaped undersurface 56. These methods include the addition of a boss of material having a convex shape to the bottom of the top surface or, in the alternative, the formation of the convex shape can be formed on the mold.

FIG. 2 shows the inclined vial holder 20 with the flat top support 32 and the flat bottom support 40 in a quiescent position with the flat bottom 40 being slightly bent toward the flat top support 32 such, that displacement of the flat bottom portion 40 from the flat top support 36 produces a resilient clamping force therebetween.

FIG. 3 shows, in the end view, the slight bending of the flat bottom portion 40 towards the flat top portion 32 to produce the positive clamping force therebetween when a vial 50 is inserted therebetween, as shown in FIG. 4.

As shown in FIG. 4, the clamping action is directed along the axial length of the vial 50 such, that the clamping force is directed to hold the bottle in compression thereby avoiding the application of a clamping force upon the neck 62 of the vial 50 which is the weakest portion of the vial 50. The indentation 56 cooperates with the bottom 60 of vial 50 to urge the shoulder of the vial 50 against the flat bottom support 40.

FIG. 5 shows the flat bottom support 40 having the aperture 46 formed therein which is adapted to permit the top 64 of a vial 50 to pass therethrough to the outer edge of the flat bottom support 40. The top 64 of the vial 50 is adapted to extend through the aperture 46 in the flat bottom support 40 so as to be freely supported at said acute angle beyond the surface of the flat bottom support 40.

FIG. 6 shows the flat top surface 32 which has an indentation 56 which is adapted to cooperate with the bottom 60 of the vial 50, as shown in FIG. 4.

FIG. 7 shows the inclined vial holder 20 attached to a vertical supporting surface, such as wall 62. The vertical backplate 26 has fasteners 64 and 66 passing through opening 54 to fixedly secure the holder 20 to the wall 62. The vial 50 is held in a clamped fixed position at an inverted inclined angle. The level of fluid 68 in the vial 50 remains in a substantially horizontal plane relative to the vertical backplate 26.

FIG. 8 shows the relationship between the flat bottom support 40 and the top 66 of vial 50 which extends through the aperture 46. The shoulder of vial 50 is urged against the chamfered edge 48, shown in FIG. 1, to support the vial in the inverted inclined position to permit the top 64 to extend freely through the aperture 46 and beyond the flat bottom support 40.

In FIG. 8, a user can insert the hypodermic needle 80 or a syringe 82 into and through a sealable top 64 into the interior of vial 50 to remove a proper dosage or volume of fluid from vial 50.

When the level of fluid 68 reaches the neck 62, the horizontal level of the fluid 68 in the neck 62 is determined by the acute angle between the coplanar flat top support 32 and flat bottom support 40. The acute angle measure from a horizontal plane which is normal to the vertical backplate 26 is in order of about 15° to about 45°. In the preferred embodiment, the acute angle is 30°.

The vial 50, when substantially empty, is removed by a user grasping the vial 50 and withdrawing the same from the holder 20 such, that neck 62 is guided by the elongated slot 42.

A full vial is inserted by placing the neck 62 into the elongated slot 42 and pushing the same towards the vertical backplate 26 which causes the flat bottom support 40 to be pushed away from the flat top support 32 to produce the clamping force therebetween.

When neck 62 reaches aperture 46, the top 64 passes through the aperture which causes the shoulder of the vial to engage the flat bottom support 40. The neck 62 is located within aperture 46 and the top 64 freely extends from the holder. The clamping force developed between the flat top support 32 by indentation 56 and the flat bottom support 40, holds the vial in an inverted inclined angle which is easily accessible with a syringe 82.

In the preferred embodiment, the inclined vial holder is fabricated of a plastic material. Although the preferred embodiment is that of a unitary or integral holder formed from a single construction, it is envisioned that the holder could be formed of several elements fabricated and assembled so as to function as an integral unit. Also, a plurality of individual units may be attached to a common vertical back member to hold several vials.

What is claimed is:

1. A holder for supporting a vial having a top, neck, shoulder and bottom and which has a fluid therein, said vial being held in an inverted position with the top thereof being held at an inclined angle, said holder comprising a vertical backplate having a top edge and a bottom edge and being adapted to be fastened to a vertical supporting surface;

a relatively flat top support fastened to the top of said vertical backplate and extending therefrom at a predetermined acute angle, as measured from a horizontal plane normal to the intersection of the top edge of the vertical backplate and the relatively flat top support, said flat top support having a length which is greater than the width of a vial to be supported thereby;

a relatively flat bottom support fastened to the bottom edge of said vertical backplate and extending therefrom at substantially said acute angle from a horizontal plane normal to the intersection of the vertical backplate and relatively flat bottom support, said flat bottom support having a length which extends from the intersection of the flat bottom support with the edge of the vertical backplate to an outer edge located at the intersection of the flat bottom support with a plane which is normal to the end of the flat top support, said flat bottom support having an elongated slot with a width adapted to receive a neck of a said vial and which extends from the outer edge of the flat bottom support to substantially the center of the planar flat bottom support, said flat bottom support having an aperture which extends through the flat bottom surface and which has the center thereof in alignment with the center of the planar flat top support and a diameter which is slightly greater than the diameter of a top of a said vial adapted to be supported thereby, said aperture communicating with the elongated slot to enable a top of a vial to be passed through the aperture wherein a top of a said vial is adapted to extend therethrough and be freely supported at said acute angle beyond the surface of the flat bottom support, said flat bottom surface having means defining inwardly sloping walls around the periphery of the apertures and elongated slot on the side of the flat bottom support adjacent the flat top support;

said flat top support and said flat bottom support being adapted to removably receive a vial inserted therebetween in an inverted position with a said neck of a said vial being first positioned in the elongated slot and urged toward the vertical backplate until a said neck of a said vial communicates with said aperture whereupon the flat top support and flat bottom surface cooperate to a clamping force between a said bottom and a shoulder of a said vial to hold a said vial in a fixed inclined angle with a top of a said vial freely extending therefrom and adapted to have a user insert a syringe therein to remove fluid from said vial being held in an inclined angle.

2. The vial holder of claim 1 wherein the flat bottom surface wall defining means includes means for defining a chamfered edge around the periphery of the aperture and elongated slot on the side of the flat bottom support adjacent the flat top support, said chamfered edges being adapted to receive and communicate with a said vial to engage and support a said vial against the flat bottom support in response to a clamping force developed therebetween which urges a said vial into a tight supporting relationship against the edge of the aperture.

3. The inclined vial holder of claim 2 wherein the acute angle is selected to be between about 15° to about 45°.

4. The inclined vial holder of claim 3 wherein the acute angle is selected to be about 30°.

5. The inclined vial holder of claim 2 wherein the vertical backplate, flat top support, and flat bottom support are an integral device fabricated from a plastic material.

6. The inclined vial holder of claim 2 wherein the flat top support includes means for defining an indentation therein at approximately the center of the flat top surface and extending therefrom toward the flat bottom support, said indentation being adapted to be received and to communicate with a said bottom of a said vial to produce a clamping force between said indentation and chamfered edge of the aperture to firmly support a said vial at an inclined angle.

7. The inclined vial holder of claim 6 further including means for fastening the vertical backplate to a vertical supporting surface.

8. The inclined vial holder of claim 2 wherein said inclined angle is selected to position the fluid in the neck of a said vial such, that when only a small quantity of fluid remains in a said vial, such remaining fluid substantially fills the neck of a said inclined inverted vial to enable a user to insert a syringe therein to remove substantially all of the fluid from a said vial.

9. In combination, a unitary holder for supporting a vial having a neck, top, shoulder, and a bottom wherein the vial contains a sterile fluid therein, said vial being adapted to be supported at an inclined angle, said holder comprising a vertical back member adapted to be fastened to a vertical supporting surface;

a planar top support which is joined to said vertical back member and which extends therefrom at a predetermined acute angle as measured from a horizontal plane normal to the intersection of the vertical back member, said planar top support having a length which is greater than the width of the vial supported thereby, and which terminates in an outer edge, said planar top support being adapted to slideably engage and support a bottom of the vial and having a sufficient resiliency to produce a clamping force thereagainst;

a planar bottom support which extends from said vertical back member at substantially said acute angle from a horizontal plane normal to the intersection of the vertical backplate and being in substantial spaced parallel alignment with the planar top support when the vial is positioned therebetween, said planar bottom support having a length which extends from the vertical back member to a line defined by the intersection of the planar bottom support with a plane which is normal to the end of the planar top support, said planar bottom support defining an elongated slot having a width which is adapted to receive the neck of the vial, said elongated slot extending from the outer edge of the planar bottom support to a point substantially in alignment with the center of the planar bottom support, said planar bottom support having an aperture therein which extends therethrough and which has a center thereof in alignment with the center of the planar top support, said aperture having a diameter which is slightly greater than the diameter of the neck of the vial adapted to be supported thereby, said aperture communicating with the elongated slot to enable a top of the vial to be passed from the outer edge of the planar bottom support through the elongated slot into the aperture, said planar bottom support having means defining inwardly sloping walls around the periphery of the apertures and elongated slot on the side of the planar bottom support adjacent the planar top support;

said planar top support and said planar bottom support removably clamping the vial therebetween by means of the clamping force between the bottom and shoulder of the vial to hold the said vial in a fixed inclined angle with a top of the vial freely extending therefrom and adapted to have a user insert a syringe therein to remove sterile fluid from the vial being held in an inclined angle.

10. The combination of claim 9 wherein the planar bottom surface includes means for defining a chamfered edge around the periphery of the aperture and elongated slot on the side of the planar bottom support adjacent the planar top support, said chamfered edges being adapted to receive and communicate with the vial to engage and support the vial against the planar bottom support in response to a clamping force developed therebetween which urges the vial into a tight supporting relationship against the edge of the aperture.

11. The combination of claim 9 wherein the acute angle is selected to be between about 15° to about 45°.

12. The combination of claim 11 wherein the acute angle is selected to be about 30°.

13. The combination of claim 9 wherein the unitary holder is fabricated from a plastic material.

14. The combination of claim 9 wherein the planar top support wall defining means includes means for defining a convex shaped surface at approximately the center of the planar top surface and extending therefrom toward the planar bottom support, said convex shaped surface being adapted to be received and to communicate with the bottom of the vial to produce a clamping force between said convex shaped surface and chamfered edge of the aperture to firmly support the vial at an inclined angle.

15. The combination of claim 6 further including means for fastening the vertical backplate to a vertical supporting surface.

16. The combination of claim 9 wherein said inclined angle is selected to position the fluid in the neck of the vial such, that when only a small quantity of fluid remains in the vial, such remaining fluid substantially fills the neck of the inclined inverted vial to enable a user to insert a syringe therein to remove substantially all of the fluid from the vial.

* * * * *